(12) United States Patent
Hsiao-Ping et al.

(10) Patent No.: US 7,857,944 B2
(45) Date of Patent: Dec. 28, 2010

(54) METHOD AND APPARATUS FOR ESTERIFICATION

(75) Inventors: Huang Hsiao-Ping, Taipei (TW); Yu Cheng-Ching, Taipei (TW); Lee Ming-Jer, Taipei (TW); Hung Shih-Bo, Taipei (TW); Lai I-Kuan, Taipei (TW)

(73) Assignee: National Taiwan University, Taipei (TW)

( * ) Notice: Subject to any disclaimer, the term of this patent is extended or adjusted under 35 U.S.C. 154(b) by 877 days.

(21) Appl. No.: 11/789,880

(22) Filed: Apr. 25, 2007

(65) Prior Publication Data
US 2008/0264772 A1 Oct. 30, 2008

(51) Int. Cl.
*B01D 3/00* (2006.01)
*B01J 8/02* (2006.01)
*B01J 35/02* (2006.01)

(52) U.S. Cl. .................. 202/154; 202/155; 202/158; 202/172; 202/182; 202/186; 422/192; 422/212; 422/218; 422/222; 422/261; 261/114.5

(58) Field of Classification Search ......... 202/153–155, 202/158, 161, 172–173, 179, 182, 186, 197; 203/29, 41, 78, 80, 84, 87, DIG. 6; 422/190–192, 422/211–212, 218, 222, 261; 261/114.5
See application file for complete search history.

(56) References Cited

U.S. PATENT DOCUMENTS

| | | | | | |
|---|---|---|---|---|---|
| 5,008,046 A | * | 4/1991 | Bremus et al. | ............... | 554/170 |
| 5,593,548 A | * | 1/1997 | Yeoman et al. | ............... | 203/29 |
| 5,945,560 A | * | 8/1999 | Iffland et al. | ................. | 560/205 |
| 6,028,215 A | * | 2/2000 | Bessling et al. | ............. | 560/265 |
| 6,500,309 B1 | * | 12/2002 | Tung | ........................... | 202/153 |
| 6,730,806 B2 | * | 5/2004 | Wu et al. | ...................... | 560/254 |
| 2006/0264674 A1 | * | 11/2006 | Banning et al. | ............. | 564/443 |
| 2009/0264674 A1 | * | 10/2009 | Huang et al. | ................. | 560/204 |

OTHER PUBLICATIONS

Bock, Heiko et al., "Analysis of Reactive Distillation using the Esterification of Acetic Acid as an Example", Chemical Engineering Technology 20, Jan. 1, 1997, pp. 182-191.
D.B. Keyes, "Esterification Processes and Equipment", Industrial and Egineering Chemistry vol. 24 No. 10, Oct. 1, 1932, pp. 1096-1103.

* cited by examiner

*Primary Examiner*—Virginia Manoharan
(74) *Attorney, Agent, or Firm*—Haverstock & Owens LLP

(57) ABSTRACT

The method and apparatus for improving the esterification procedure, in particular for improving the esterification procedure to obtain an ester of low carbon number such as the ethyl acetate and the isopropyl acetate, are provided. By applying the provided method and apparatus, the conversion ratio of the esterification procedure is significantly increased and hence an ester product of a relatively high purity, up to the industrial specification, is obtained.

20 Claims, 1 Drawing Sheet

METHOD AND APPARATUS FOR ESTERIFICATION

FIELD OF THE INVENTION

The present invention relates to a method for esterification and the apparatus therefor. More particularly, the present invention relates to a method for producing an ester of a relatively high purity and the apparatus therefor.

BACKGROUND OF THE INVENTION

Ethyl acetates and isopropyl acetates are solvents of great importance in the industry, which are commonly utilized for plastics, oils, printing inks and materials for synthesized perfumes. Nowadays, the processes for producing the ethyl acetate could be typically classified as follows:

(i) The process proposed by Keyes (1932) involves an esterification reaction of acetate in a pre-reactor and plural purification and recycling procedures of the ester product in plural strippers and separation devices. Such process, however, is relatively complicated owing to a bit more reaction units involved therein, and is hence disadvantageous in system operation and maintenance.

(ii) There are plenty of researches studying the single reactive distillation (RD) column designed process. Such process is carried out with a typical RD column, which is principally divided into three sections including the reaction section, the purification section and the stripping section, and therein the esterification reaction is promoted with a homogeneous or a non-homogenous catalyst. The single RD column designed process for ethyl acetate is firstly proposed by Suzuki et al. in 1972, where the operation and control of the RD column for an ethyl acetate system is mentioned. Nevertheless, in such a process, the purity of the ester product obtained at the top section of RD column is not high enough, and the product obtained at the bottom section of RD column, containing four different contents, still needs to be further processed. The data in those researches show that the ethyl acetate product obtained in such an RD column has a relatively low purity, and thus fails to meet the current industrial demands. Typically, the product obtained at the top section of such RD column is restricted by the acid-alcohol-ester azeotrope, and the product obtained at the bottom section thereof is restricted by the high boiling point of acetate. Accordingly, it may need to discharge or further process the undesired product. As disclosed in U.S. Pat. No. 6,693,213, for example, on one hand the organic product obtained at the top section of RD column needs to be separated and is then discharged therefrom, and on the other hand, the reactant of acid, with a high purity, needs to be recycled at the bottom section of RD column, both bringing disadvantageous in the esterification process and the energy consumption.

The process proposed by Bock (1997) is based on a design of two distillation columns, including an RD column and a stripper. In this case, it is possible to obtain the ethyl acetate with a relatively high purity at the bottom of the second column, i.e. the stripper, while the mixture of acid-alcohol-ester azeotrope obtained at the top thereof needs to be directed back to the first column, i.e. the RD column, to be processed, and the mixture of alcohol and water, that is obtained at the bottom of RUD column, also needs to be further treated.

For overcoming the mentioned drawbacks existing in the conventional techniques, a novel method and apparatus for the esterification is provided in the present invention.

SUMMARY OF THE INVENTION

It is one aspect of the present invention to provide a method and apparatus for producing an ester with a relatively high purity.

It is a further aspect of the present invention to provide a method and apparatus for esterification, where the procedures for ester separation involved therein are designed with respect to the thermodynamic characteristics of different separation systems.

It is still a further aspect of the present invention to provide a method and apparatus for esterification, whereby the obtained ester product could meet the current industrial demands.

In accordance with the mentioned aspect, the provided method includes the steps of (a) feeding and mixing an acid and an alcohol in a bottom section of a reactive distillation column having a solid catalyst therein so as to produce a first vapor mixture, (b) directing the first vapor mixture out from the reactive distillation column and cooling the first vapor mixture to obtain an aqueous mixture therefrom, (c) separating the aqueous mixture with a separation device to isolate a first aqueous mixture and a second aqueous therefrom, (d) directing a first portion of the first aqueous mixture into the reactive distillation column, (e) purifying a second portion of the first vapor aqueous mixture to obtain an ester product of a relatively high purity and a second vapor mixture, (f) cooling the second vapor mixture to obtain a third aqueous mixture, and (g) directing the third aqueous mixture back into the separation device for further purifying the third aqueous mixture.

Preferably, the provided method is performed under a pressure ranged in 1~2 atm, in which the step (a) is carried out at a temperature ranged in 70~125° C., the step (c) is carried out at a temperature ranged form a room temperature to 50° C., and the step (e) is carried out at a temperature ranged in 75~95° C.

Preferably, the solid catalyst is an ionic exchange resin.

Preferably, the reactive distillation column comprises plural rectifying trays and plural reacting trays.

Preferably, the number of the rectifying trays is ranged from 5 to 15, and the number of the reacting trays is ranged from 8 to 20.

Preferably, the acid and the alcohol react with each other at the bottom section of the reactive distillation column.

Preferably, the molar ratio of the acid to the alcohol is ranged from 1.0:1.1 to 1.0:1.0.

Preferably, the acid is an acetic acid, and the alcohol is one selecting from a group consisting of an ethanol, an isopropanol and a butanol.

Preferably, the first aqueous mixture obtained in the step (c) is an organic-rich mixture and the second aqueous is a water-rich mixture.

Preferably, in the step (d), the first portion of the first aqueous mixture is directed into the reactive distillation column by a T-typed bypass.

Preferably, in the step (e), the second portion of the first aqueous mixture is directed into a stripper for being further purified.

In accordance with the mentioned aspect, the provided apparatus is constructed by a reactive distillation column, a solid catalyst filled therein, a separation device, a stripper and a T-typed bypass.

In accordance with the mentioned aspect, the reactive distillation column includes a bottom section with a first feed port for feeding an acid thereinto and a second feed port for feeding an alcohol thereinto, and includes a top section with a first discharge port and a third feed port, wherein the acid and the alcohol react with each other in the bottom section and a vapor mixture is obtained thereby. The solid catalyst is filled in the bottom section and a middle section of the reactive distillation column, or a middle-to-top section of the reactive distillation column. The separation device includes a fourth feed port coupled to the first discharge port, a fifth feed port, a second discharge port and a third discharge port. The stripper includes a fourth discharge port and a sixth feed port, wherein the fourth discharge port is located at the bottom of the stripper and is coupled to the fifth feed port. The T-typed bypass has a first end coupled to the third feed port, a second end coupled to the second discharge port and a third end coupled to the sixth feed port.

In accordance with the mentioned aspect, the vapor mixture is cooled and therefrom an aqueous mixture is formed. The aqueous mixture is directed into the separation device so as to isolate an organic-rich aqueous mixture therefrom. The organic-rich aqueous mixture has a first portion directed back into the top section through the third feed port and a second portion directed into the stripper through the T-typed bypass and the sixth feed port, so as to be purified therein and thereby an ester product of a relatively high purity is obtained at the fourth discharge port.

Preferably, the reactive distillation column further includes plural reacting trays configured in the bottom section and plural rectifying trays configured between the top section and the middle section.

Preferably, the number of the rectifying trays is ranged from 5 to 15, and the number of the reacting trays is ranged from 8 to 20.

Preferably, the solid catalyst is an ionic exchange resin.

Preferably, the solid catalyst is filled in the reactive distillation column with a ratio of the fill amount for the reacting trays to the fill amount of the rectifying trays ranged in 1~100, and more preferably, in 1~10.

Preferably, the solid catalyst is filled in the reactive distillation column with a ratio of the fill amount for the bottom section to the fill amount of the middle section and the middle-to-top section of 10.

Preferably, the molar ratio of the acid to the alcohol is ranged from 1.0:1.1 to 1.0:1.0.

Preferably, the acid is an acetic acid, and the alcohol is one selecting from a group consisting of an ethanol, an isopropanol and a butanol.

Preferably, the apparatus is operated under a pressure ranged in 1~2 atm.

Preferably, the apparatus further includes a first boiler and a second boiler respectively coupled to an external side of the bottom section and an external side of the bottom of the stripper.

Preferably, the reactive distillation column is operated at a temperature ranged in 70~125° C.

Preferably, the separation device is operated at a temperature ranged from a room temperature to 125° C.

Preferably, the stripper is operated at a temperature ranged in 75~95° C.

Preferably, the vapor mixture has a composition approaching to an alcohol-water-acetate azeotrope.

Preferably, the apparatus further includes a first condenser coupled between the first discharge port and the fourth feed port, and a second condenser coupled between the fourth discharge port and the fifth feed port.

Preferably, the stripper farther includes a fifth discharge port and thereby the ester product is directed out.

Preferably, the apparatus further includes an ester reservoir coupled to the fifth discharge port for collecting the ester product.

Preferably, the apparatus further includes a water reservoir coupled to the third discharge port for collecting a water-rich product separated by the separation device.

The foregoing and other features and advantages of the present invention will be more clearly understood through the following descriptions with reference to the drawings, wherein:

DETAILED DESCRIPTION OF THE PREFERRED EMBODIMENT

Figure 1:
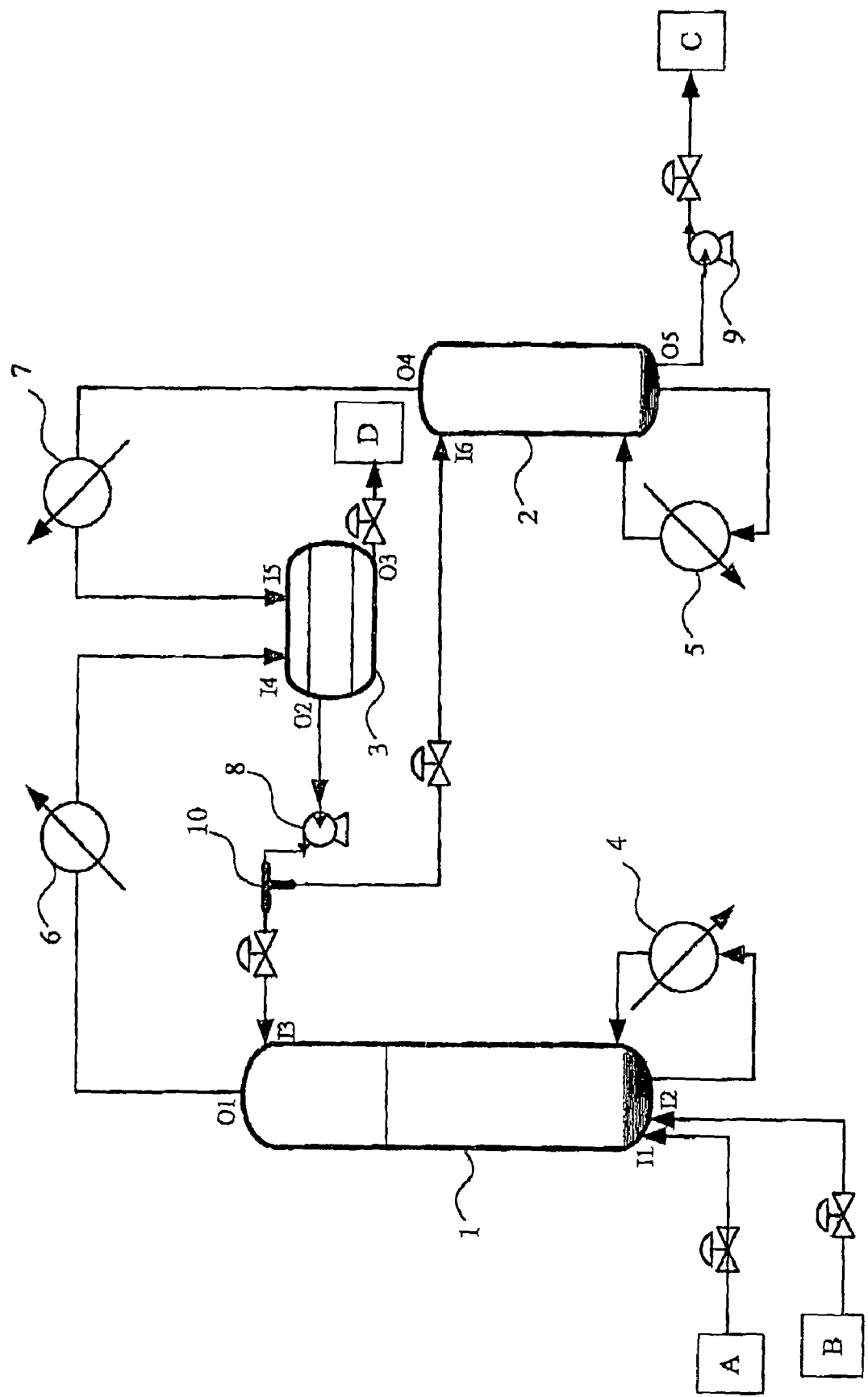
FIG. 1 is a diagram illustrating the apparatus for the esterification and the relevant procedures therefor in accordance with a preferred embodiment of the present invention.

The present invention will now be described more specifically with reference to the following embodiments. It is to be noted that the following descriptions of preferred embodiments of this invention are presented herein for purpose of illustration and description only; it is not intended to be exhaustive or to be limited to the precise form disclosed.

According to the present invention, the apparatus for producing the ester is aimed to the design of the reactive distillation (RD) column for the esterification. The esterification is typically shown as follows:

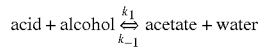

$$\text{acid} + \text{alcohol} \underset{k_{-1}}{\overset{k_1}{\rightleftharpoons}} \text{acetate} + \text{water}$$

The esterification is a reversible reaction, wherein the acetate may be ethyl acetate or isopropyl acetate, the acid may be acetic acid, and the alcohol may be ethanol or isopropanol. The catalyst typically used in this reaction may be a homogeneous one or a non-homogeneous one. Preferably, the non-homogeneous catalyst, i.e. a solid catalyst, is adopted in the RD column according to the present invention. Since the solid catalyst could be arranged in any section, e.g. the bottom section and the top section, of the RD column by means of filling, it is able to select any desired section of the RD column for the reaction. Moreover, an essential recycling procedure while the liquid catalyst is adopted could be accordingly prevented. Typically, the ionic exchange resin is adoptable for the solid catalyst, which could be filled in a common type of package or could be fixedly arranged in the column.

The boiling points of the respective contents involved in an ethyl acetate system are listed in the following TABLE 1.

TABLE 1

| Contents | Boiling Point (° C.) |
|---|---|
| EtOH/EtAc/H$_2$O | 70.09 |
| EtAc/H$_2$O | 70.37 |
| EtOH/EtAc | 71.81 |
| EtAc | 77.20 |
| EtOH/H$_2$O | 78.18 |
| EtOH | 78.31 |
| H$_2$O | 100.0 |
| HAc | 118.01 |

The azeotrope contents include an alcohol-acetate-water azeotrope and an acetate-water, an alcohol-acetate and an alcohol-water azeotrope, where the existence of azeotropes may bring a limitation to separation on the distillation edge. Among the mentioned contents, the mixture of alcohol-acetate-water azectrope (EtOH/EtAc/$H_2O$) has a lowest boiling point of 70.09° C. and is hence regarded as a light content, while the heavy content, acetic acid (HAc), has a highest boiling point of 118.01° C. In a typical RD column, the mixture obtained at the top thereof has a composition approaching to the alcohol-acetate-water azeotrope, and the product obtained at the bottom thereof is acetic acid. The desired product, ethyl acetate, has a boiling point of 77.2° C., which is ranged between those of the respective alcohol-acetate-water azeotrope and acetic acid, and this is why the product obtained from the conventional single RD column would has a relatively low purity.

Furthermore, the boiling points of the respective contents involved in an ethyl acetate system are listed in the following TABLE 2. It is apparent that, the esterification system for isopropyl acetate has the same limitation in distillation so that the desired product having a middle-ranged boiling point is difficult to be obtained therefrom.

TABLE 2

| Contents | Boiling Point (° C.) |
| --- | --- |
| IPA/IPAc/$H_2O$ | 74.22 |
| IPAc/$H_2O$ | 76.57 |
| IPA/IPAc | 78.54 |
| IPAc | 80.06 |
| IPA/$H_2O$ | 82.35 |
| IPA | 88.52 |
| $H_2O$ | 100.0 |
| IPAc | 118.01 |

The apparatus for esterification according to the present invention is constructed by an RD column, a separation device and a stripper, where the RD column is only divided into a purification section and a reaction section. The reaction section is referred to the section in which the trays are filled with solid catalysts, and is arranged in a region between a middle section, or a middle-to-upper section, and a bottom section of the RD column. The purification section is arranged above the reaction section. The reactants, including the acetic acid and the alcohol, are fed into the column at the bottom thereof, or fed through a re-boiler. Since the great amount of heavy content, the acid with a high purity, would remain at the bottom inside the column, it needs to arrange the catalyst at the bottom section, with an filling amount greater than 10~100 times of that in the reaction section, so as to improve the reaction of the acetic acid and alcohol. The alcohol is excessively fed into the column, with an alcohol-to-acid ratio ranged from 1:0.94 to 1:0.96, preferably. The product obtained from the mentioned reaction, having a composition approaching the alcohol-acetate-water azeotrope, is condensed in the separation device, so as to isolate the organic phase of the product from the water phase thereof.

In the mentioned aspect, the present invention provides a complete distillation process for esterification of ethyl acetate and isopropyl acetate. The apparatus for carrying such a process includes an RD column, a separation device and a stripper. The RD column is divided into a purification portion and a reaction portion, and the reactants are fed into the RD column at the bottom section thereof. The reaction portion of the RD column is filled with the solid catalyst. The mixture of alcohol-acetate-water azeotrope obtained at the top section of RD column is directed into the separation device for being separated, and then a portion of organic phase thereof is refluxed to the top section of RD column while a further portion of organic phase thereof is directed to the stripper so as to obtain an ester product with a relatively high purity at the bottom of stripper.

Please refer to FIG. 1, which is a diagram illustrating the apparatus for the esterification and the relevant procedures therefor in accordance with a preferred embodiment of the present invention. With reference to FIG. 1, the procedures of the method for esterification according to the preferred embodiment of the present invention are illustrated.

According to the present invention, the apparatus for esterification for producing an ester with a relatively high purity includes an RD column 1, a stripper 2 and a separation device 3. Preferably, the apparatus is further provided with a first condensing system of a first condenser 6 and its relevant pipes for connecting the RD column 1 with the separation device 3. The apparatus also includes a second condensing system of a second condenser 7 and its relevant pipes, so as to connect the stripper 2 with the separation device 3.

Furthermore, the apparatus according to the present invention includes a first re-boiler 4 configured at the bottom of RD column 1 and a second re-boiler 5 configured at the bottom of stripper 2. The stripper 2 is further connected to an ester reservoir C at the bottom thereof, and the separation device 3 is further connected to a water reservoir D at the water-phase side thereof.

The top section of RD column 1 is connected to the organic-phase side of separation device 3 through a reflux system of a first pump 8, a T-typed bypass 10 and the relevant pipes. A second pump 9 is additionally configured to connect the ester reservoir C to the stripper 2.

The organic-phase obtained from the separation device 3 is partially bypassed through the reflux system into the stripper 2 with the T-typed bypass 10.

As shown in FIG. 1, the acid A and the alcohol B of a specific purity are fed into the RD column 1 at the bottom section thereof, respectively. For example, in an ethyl acetate system, the acid A is acetic acid and the alcohol B is ethanol. In more specifics, the acid A and the alcohol B are respectively fed into the RD column 1 through a first feed port I1 and a second feed port I2 at the bottom thereof, and a vapor mixture, i.e. the unpurified alcohol-acetate-water azeotrope, is obtained from the reaction of the acid A and the alcohol B. The vapor mixture is directed out through the discharge port O1 at the top section of RD column 1, condensed with the first condenser 6, and is then directed into the separation device 3 through the feed port I4 for being phase-separated. Moreover, the unpurified mixture of alcohol-acetate-water azeotrope, that is obtained at the discharge port O4 at the top section of separation device 2 is condensed with the second condenser 7, and is then directed into the separation device 3 through the feed port I5 for being phase-separated. After the phase-separation, the water-rich phase of the mixture, i.e. the lower layer, is discharged at the discharge port O3 from the separation device 3, and is directed into the water reservoir D. The organic phase of the mixture, i.e. the upper layer, is pumped by the pump 8 at the discharge port O2 and divided into two organic-phase flows by the T-typed bypass 10, where the principal one thereof is directed into the top section of RD column at the feed port I3 through the pump 8 and the T-typed bypass 10, and the remaining one is directed into the top section of stripper 2 at the feed port I6 through the pump 8 and the T-typed bypass 10.

The vapor mixture obtained from the mentioned reaction, including the product of ester and water and some alcohol, is directed out of the RD column at the discharge port O1, directed into the condenser 6 for being liquefied, and then directed into the separation device 3 for being phase-separated. It is worthy to note that, in the apparatus and method according to the present invention, no flow of product or substance is discharged at the bottom section of RD column 1.

The tray temperature of the RD column 1 is controlled with the volume ratio of feeds and the re-boiler configured at the bottom thereof, and the tray temperature of the stripper 2 is also controlled with the re-boiler configured at the bottom thereof.

For saving the process cost, according to the present invention, the solid catalyst is filled in the region between the middle-to-top section and the bottom section, or filled in the region between the middle section and the bottom section, with the ratio of the fill amount for reacting trays to that of rectifying trays ranged in 1~100, and 1~10 preferably. According to the present invention, the conventional commercial catalysts are adoptable in the method and apparatus.

In the present invention, the operating temperature of the RD column 1 is selectable, depending on the desired product system. According to the preferred embodiment, the operating temperature is ranged in 70° C.~125° C. for an ethyl acetate system, and is ranged in 75° C.~125° C. for an isopropyl acetate system. Furthermore, the operating temperature of the stripper 2 is ranged in 70° C.~90° C. for an ethyl acetate system, and is ranged in 75° C.~100° C. for an isopropyl acetate system. Typically, the operating temperature of the separation device 3 is ranged from the room temperature to 50° C.

According to the preferred embodiment of the present invention, the RD column 1 and the stripper 2 of the ethyl acetate system and the isopropyl system are operated under a pressure ranged in 1~2 atm, while the separation device 3 is operated under the normal pressure.

In the present invention, the molar feed ratio of the acid to the alcohol is adjusted through the variation of feed volume of acid, with the range of 0.9~1.0.

According to the present invention, since the acid and the alcohol are reacting in the liquid phase, the product of ester and water is directed into the respective top sections of RD column 1 and stripper 2. For increasing the reaction conversion, the unreacting liquid alcohol, in combination with the ester and water, would be refluxed to the top section of RD column 1 for a further reaction.

According to the preferred embodiment of the present invention, the amount of rectifying trays configured in the RD column 1 is ranged in 1~15, the amount of reacting trays is ranged in 8~20, and the amount of stripping trays configured in the stripper 2 is ranged in 5~15.

Example 1

In an ethyl acetate system, the molar feed ratio of the acetic acid to the ethanol is 0.9652, the operating temperature of the RD column is ranged in 75° C.~23° C., the operating temperature of the condenser of the RD column is 70° C., the operating temperature of the stripper is ranged in 75° C.~85 C, and the operating temperature of the condenser of the stripper is 70° C. In this case, a commercial catalyst of Porulite CT 179 is adopted in this case. The result is listed in the following TABLE 3.

Example 2

In an isopropyl acetate system, the molar feed ratio of the acetic acid to the isopropanol is 0.944, the operating temperature of the RD column is ranged in 80° C.~118° C., the operating temperature of the condenser of the RD column is 74.2° C., the operating temperature of the stripper is ranged in 79° C.~95 C, and the operating temperature of the condenser of the stripper is 74.2° C. In this case, a commercial catalyst of Amerlyst® 15 or Amerlyst® 35 is adopted in this case. The result is also listed in the following TABLE 3.

TABLE 3

| | System | | | |
| --- | --- | --- | --- | --- |
| | Ethyl Acetate (Example 1) | | Isopropyl Acetate (Example 2) | |
| Item | RD Column | Stripper | RD Column | Stripper |
| Total No. of Trays | 20 | 10 | 24 | 8 |
| No. of Stripping Trays | | 9 | | 7 |
| No. of Reacting Trays | 11 | | 14 | |
| No. of Rectifying Trays | 9 | | 10 | |
| Feeding of Acetic Acid | Bottom | | Bottom | |
| Feeding of Alcohol | Bottom | | Bottom | |
| Feed Concentration of Acetic Acid (Molar Ratio) | 0.95 | | 0.95 | |
| Feed Concentration of Alcohol (Molar Ratio) | 0.87 | | 0.6491 | |
| Molar Feed Ratio of Acid to Alcohol | 0.9652 | | 0.944 | |
| Concentration of Ester (Molar Ratio) | | 0.99000 | | 0.99000 |
| Temperature of the Separation Device (° C.) | 40 | | 50 | |

Based on the mentioned, the present invention provides a method and apparatus for esterification, where the procedures for ester separation involved therein are designed with respect to the thermodynamic characteristics of different separation systems. Therefore, the present invention not only has the novelty and the progressiveness, but also has an industry utility.

While the invention has been described in terms of what is presently considered to be the most practical and preferred embodiment, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

What is claimed is:

1. An apparatus for producing an ester, comprising:
   a reactive distillation column having a bottom section with a first feed port for feeding an acid thereinto and a second feed port for feeding an alcohol thereinto, and having a top section with a first discharge port and a third feed port, wherein said acid and said alcohol react with each other in said bottom section and thereby a vapor mixture is obtained;
   a solid catalyst filled in said bottom section and one of a middle section of said reactive distillation column and a middle-to-top section of said reactive distillation column;
   a separation device having a fourth feed port coupled to said first discharge port, a fifth feed port, a second discharge port and a third discharge port;
   a stripper having a top, a bottom, a fourth discharge port, a fifth discharge port and a sixth feed port, wherein said fourth discharge port is located at said top of said stripper and is coupled to said fifth feed port, and said fifth discharge port is located at said bottom of said stripper; and a T-typed bypass having a first end coupled to said third feed port, a second end coupled to said second discharge port and a third end coupled to said sixth feed port;

wherein said vapor mixture is cooled and therefrom an aqueous mixture is formed, said aqueous mixture is directed into said separation device so as to isolate an organic-rich aqueous mixture therefrom, said organic-rich aqueous mixture has a first portion directed back into said top section through said third feed port and a second portion directed into said stripper through said T-typed bypass and said sixth feed port so as to be purified therein, and thereby an ester product is obtained at said fifth discharge port of said stripper.

2. The apparatus as claimed in claim 1, wherein said reactive distillation column further comprises:

plural reacting trays configured in said bottom section; and plural rectifying trays configured in said top section and said middle section of said reactive distillation column.

3. The apparatus as claimed in claim 2, wherein the number of said rectifying trays is ranged from 5 to 15.

4. The apparatus as claimed in claim 2, wherein the number of said reacting trays is ranged from 8 to 20.

5. The apparatus as claimed in claim 2, wherein said solid catalyst is an ionic exchange resin.

6. The apparatus as claimed in claim 5, wherein said solid catalyst is filled in said reactive distillation column with a ratio of the fill amount for said reacting trays to the fill amount of said rectifying trays ranged in 1~10.

7. The apparatus as claimed in claim 5, wherein said solid catalyst is filled in said reactive distillation column with a ratio of the fill amount for said bottom section to the fill amount of said middle section and said middle-to-top section of 10.

8. The apparatus as claimed in claim 1, wherein the molar ratio of said acid to said alcohol is ranged from 1.0:1.1 to 1.0:1.0.

9. The apparatus as claimed in claim 1, wherein said acid is an acetic acid.

10. The apparatus as claimed in claim 1, wherein said alcohol is one selected from a group consisting of an ethanol, an isopropanol and a butanol.

11. The apparatus as claimed in claim 1, operated under a pressure ranged in 1~2 atm.

12. The apparatus as claimed in claim 1, further comprising a first re-boiler and a second re-boiler respectively coupled to an external side of said bottom section and an external side of the bottom of said stripper.

13. The apparatus as claimed in claim 1, wherein said reactive distillation column is operated at a temperature ranged in 70~125° C.

14. The apparatus as claimed in claim 1, wherein said separation device is operated at a temperature ranged from a room temperature to 125° C.

15. The apparatus as claimed in claim 1, wherein said stripper is operated at a temperature ranged in 75~95° C.

16. The apparatus as claimed in claim 1, wherein said vapor mixture has a composition approaching to an alcohol-water-acetate azeotrope.

17. The apparatus as claimed in claim 1, further comprising a first condenser coupled between said first discharge port and said fourth feed port, and a second condenser coupled between said fourth discharge port and said fifth feed port.

18. The apparatus as claimed in claim 1, wherein said stripper further comprises a fifth discharge port and thereby said ester product is directed out of said stripper.

19. The apparatus as claimed in claim 18, further comprising an ester reservoir coupled to said fifth discharge port for collecting said ester product.

20. The apparatus as claimed in claim 1, further comprising a water reservoir coupled to said third discharge port for collecting a water-rich product separated by said separation device.

* * * * *